(12) United States Patent
Saebo et al.

(10) Patent No.: US 7,115,759 B2
(45) Date of Patent: *Oct. 3, 2006

(54) CONJUGATED LINOLEIC ACID COMPOSITIONS

(75) Inventors: Asgeir Saebo, Eidsnes (NO); Per Christian Saebo, Volda (NO)

(73) Assignee: Natural ASA, (NO)

( * ) Notice: Subject to any disclaimer, the term of this patent is extended or adjusted under 35 U.S.C. 154(b) by 0 days.

This patent is subject to a terminal disclaimer.

(21) Appl. No.: 10/858,158

(22) Filed: Jun. 1, 2004

(65) Prior Publication Data

US 2004/0225142 A1   Nov. 11, 2004

Related U.S. Application Data

(63) Continuation of application No. 10/253,216, filed on Sep. 24, 2002, now Pat. No. 6,743,931.

(51) Int. Cl.
*C07C 51/347* (2006.01)

(52) U.S. Cl. ........................ 554/126; 554/156

(58) Field of Classification Search ................ 554/126, 554/156

See application file for complete search history.

(56) References Cited

U.S. PATENT DOCUMENTS 6,743,931 B1 * 6/2004 Sæbo et al. .................. 554/126
2004/0225142 A1 * 11/2004 Saebo et al. ................ 554/126

* cited by examiner

*Primary Examiner*—Deborah D. Carr
(74) *Attorney, Agent, or Firm*—Medlen & Carroll, LLP

(57) ABSTRACT

The present invention relates to the manufacture of conjugated linoleic acid, and in particular, to dietary supplements, feeds and food products containing conjugated linoleic acid. Accordingly, processes for producing conjugated linoleic acid of high purity and acid value are disclosed. These processes utilize alcoholate catalysts and esters of sunflower oil, safflower oil, or corn oil as the source of linoleic acid. The esters of conjugated linoleic acid produced by the process can be used in animal feeds and in food products suitable for human consumption. Furthermore, the esters can be converted into free fatty acids or incorporated into triglycerides.

16 Claims, No Drawings

CONJUGATED LINOLEIC ACID COMPOSITIONS

This application is a continuation of U.S. Ser. No. 10/253,216, filed Sep. 24, 2002, now U.S. Pat. No. 6,743,931.

FIELD OF THE INVENTION

The present invention relates to the manufacture of conjugated linoleic acid, and in particular, to feeds and food products containing conjugated linoleic acid.

BACKGROUND OF THE INVENTION

In 1978, researchers at the University of Wisconsin discovered the identity of a substance contained in cooked beef that appeared to inhibit mutagenesis. The substance was found to be a mixture of positional isomers of linoleic acid (C18:2) having conjugated double bonds. The c9,t11 and t10,c12 isomers are present in greatest abundance, but it is uncertain which isomers are responsible for the biological activity observed. It has been noted from labeled uptake studies that the 9,11 isomer appears to be somewhat preferentially taken up and incorporated into the phospholipid fraction of animal tissues, and to a lesser extent the 10,12 isomer. (Ha, et al., Cancer Res., 50: 1097 [1990]).

The biological activity associated with conjugated linoleic acids (termed CLA) is diverse and complex. At present, very little is known about the mechanisms of action, although several preclinical and clinical studies in progress are likely to shed new light on the physiological and biochemical modes of action. The anticarcinogenic properties of CLA have been well documented. Administration of CLA inhibits rat mammary tumorigenesis, as demonstrated by Birt, et al., Cancer Res., 52: 2035s [1992]. Ha, et al., Cancer Res., 50: 1097 [1990] reported similar results in a mouse forestomach neoplasia model. CLA has also been identified as a strong cytotoxic agent against target human melanoma, colorectal and breast cancer cells in vitro. A recent major review article confirms the conclusions drawn from individual studies (Ip, Am. J. Clin. Nutr., 66 (6 Supp): 1523s [1997]).

Although the mechanisms of CLA action are still obscure, there is evidence that some component(s) of the immune system may be involved, at least in vivo. U.S. Pat. No. 5,585,400 (Cook, et al., incorporated herein by reference) discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al.), incorporated herein by reference, disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066, incorporated herein by reference, describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Pat. No. 5,554,646 (Cook, et al.), incorporated herein by reference, discloses a method utilizing CLA as a dietary supplement in which pigs, mice, and humans were fed diets containing 0.5 percent CLA. In each species, a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al., incorporated herein by reference), provided data showing that incorporation of CLA into animal feed (birds and mammals) increased the efficiency of feed conversion leading to greater weight gain in the CLA supplemented animals. The potential beneficial effects of CLA supplementation for food animal growers is apparent.

Another important source of interest in CLA, and one which underscores its early commercial potential, is that it is naturally occurring in foods and feeds consumed by humans and animals alike. In particular, CLA is abundant in products from ruminants. For example, several studies have been conducted in which CLA has been surveyed in various dairy products. Aneja, et al., J Dairy Sci., 43: 231 [1990] observed that processing of milk into yogurt resulted in a concentration of CLA. (Shanta, et al., Food Chem., 47: 257 [1993]) showed that a combined increase in processing temperature and addition of whey increased CLA concentration during preparation of processed cheese. In a separate study, Shanta, et al., J. Food Sci., 60: 695 [1995] reported that while processing and storage conditions did not appreciably reduce CLA concentrations, they did not observe any increases. In fact, several studies have indicated that seasonal or interanimal variation can account for as much as three fold differences in CLA content of cows milk. (See e.g., Parodi, et al., J. Dairy Sci., 60: 1550 [1977]). Also, dietary factors have been implicated in CLA content variation, as noted by Chin, et al., J. Food Camp. Anal., 5: 185 [1992]. Because of this variation in CLA content in natural sources, ingestion of prescribed amounts of various foods will not guarantee that the individual or animal will receive the optimum doses to ensure achieving the desired nutritive effect.

Linoleic acid is an important component of biolipids, and comprises a significant proportion of triglycerides and phospholipids. Linoleic acid is known as an "essential" fatty acid, meaning that the animal must obtain it from exogenous dietary sources since it cannot be autosynthesized. Incorporation of the CLA form of linoleic acid may result in a direct substitution of CLA into lipid positions where unconjugated linoleic would have migrated. However, this has not been proven, and some of the highly beneficial but unexplained effects observed may even result from a repositioning of CLA within the lipid architecture at sites where unconjugated linoleic acid would not have otherwise migrated. It is now clear that one source of animal CLA, especially in dairy products, comes from the biochemical action of certain rumen bacteria on native linoleic acid, first isomerizing the linoleic acid to CLA, and then secreting it into the rumen cavity. Kepler, et al., J. Nutrition, 56: 1191 [1966] isolated a rumen bacterium, Butyrivibrio fibrisolvens, which catalyzes formation of 9,11-CLA as an intermediate in the biohydrogenation of linoleic acid. Chin, et al., J. Nutrition, 124: 694 [1994] further found that CLA found in the tissues of rodent was associated with bacteria, since corresponding germ-free rats produced no CLA.

In the development of a defined commercial source of CLA for both therapeutic and nutritional application, a process for generating large amounts of defined material is needed. The problem with most CLA products made by conventional approaches is their heterogeneity, and substantial variation in isoform from batch to batch. Considerable attention has been given to the fact that the ingestion of large amounts of hydrogenated oils and shortenings, instead of animal tallow, has resulted in a diet high in trans-fatty acid content. For example, Holman, et al., PNAS, 88:4830 [1991] showed that rats fed hydrogenated oils gave rise to an accumulation in rat liver of unusual polyunsaturated fatty acid isomers, which appeared to interfere with the normal metabolism of naturally occurring polyunsaturated fatty acids. These concerns were summarized in an early Editorial in *Am. J. Public Health*, 84: 722 (1974). Therefore, there exists a strong need for a biologically active CLA product of defined composition.

SUMMARY OF THE INVENTION

The present invention relates to the manufacture of conjugated linoleic acid, and in particular, to feeds and food products containing conjugated linoleic acid. In some embodiments, the present invention provides methods for producing conjugated linoleic acid with a high acid value comprising: a) providing: i) a composition comprising esters of linoleic acid; and ii) an alcoholate catalyst; b) treating the composition comprising esters of linoleic acid with the alcoholate catalyst to produce a conjugated linoleic acid ester composition; c) treating the conjugated linoleic acid ester composition with alkali to produce a saponified conjugated linoleic acid composition; and d) treating the saponified conjugated linoleic acid composition with a mild acid wash to produce a free conjugated fatty acid composition. In some embodiments, the free conjugated linoleic acid composition has an acid value of greater than 190. In other embodiments, the free conjugated linoleic acid composition has an acid value of from about 190 to 210. In still other embodiments, the mild acid wash has a pH of from about 5 to 7. In further embodiments, step (d) further comprises a plurality of mild acid washes. In some embodiments, the mild acid wash is performed with a citric acid solution. The present invention is not limited to any particular starting oil. Indeed, the composition comprising esters of linoleic acid is derived from an oil selected from the group consisting of safflower, sunflower, and corn oil. The present invention is not limited to the use of any particular-alcoholate catalyst. Indeed, the alcoholate catalyst is selected from the group consisting of sodium methylate, potassium methylate, sodium ethylate and potassium ethylate. In still other embodiments, the alcohol is ethanol.

In some embodiments, the present invention provides the conjugated linoleic acid composition produced by the method described in the preceding paragraph. In some embodiments, the composition has an acid value of greater than 190. In other embodiments, the composition has an acid value of from about 190–210. In still other embodiments, the composition is substantially free of esters of conjugated linoleic acid. In further embodiments, the composition comprises less than 1.0% trans-trans fatty acid isomers on molar basis. In some embodiments, food products or capsules comprising the conjugated linoleic acid compositions are provided.

In some embodiments, the present invention provides methods for producing conjugated linoleic acid with a high acid value comprising: a) providing: i) a composition comprising esters of linoleic acid; and ii) an alcoholate catalyst; b) treating the composition comprising esters of linoleic acid with the alcoholate catalyst to produce a conjugated linoleic acid ester composition; c) treating the conjugated linoleic acid ester composition with alkali under conditions such that a saponified conjugated linoleic acid composition comprising residual alcohol is produced; d) injecting a strong acid solution into the saponified conjugated linoleic acid composition under conditions such that an oil phase comprising free conjugated fatty acids and a water phase are produced; and e) immediately separating the oil phase and the water phase under conditions such that re-esterification between the residual alcohol and the conjugated fatty acids is substantially prevented. In some embodiments, the free conjugated linoleic acid composition has an acid value of greater than 190. In other embodiments, the free conjugated linoleic acid composition has an acid value of from about 190 to 210. In still other embodiments, the mild acid wash has a pH of from about 5 to 7. In some embodiments, the separation in step (e) is performed by centrifugal separation. In further embodiments, the strong acid solution has a pH of from about 2 to 3. The present invention is not limited to any particular starting oil. Indeed, the composition comprising esters of linoleic acid is derived from an oil selected from the group consisting of safflower, sunflower, and corn oil. The present invention is not limited to the use of any particular alcoholate catalyst. Indeed, the alcoholate catalyst is selected from the group consisting of sodium methylate, potassium methylate, sodium ethylate and potassium ethylate.

In some embodiments, the present invention provides the conjugated linoleic acid composition produced by the method described in the preceding paragraph. In some embodiments, the composition has an acid value of greater than 190. In other embodiments, the composition has an acid value of from about 190–210. In still other embodiments, the composition is substantially free of esters of conjugated linoleic acid. In further embodiments, the composition comprises less than 1.0% trans-trans fatty acid isomers on molar basis. In some embodiments, food products or capsules comprising the conjugated linoleic acid compositions are provided.

In some embodiments, the present invention provides methods of splitting saponified conjugated linoleic acids comprising: a) providing: i) a composition comprising saponified conjugated linoleic acid ii) a mild acid solution; and b) washing the composition comprising saponified conjugated linoleic acid with the mild acid solution to produce a composition comprising free conjugated linoleic acid. In some embodiments, the methods further comprise step c) repeating step (b) at least one time to produce a free conjugated fatty acid composition. In some embodiments, the free conjugated linoleic acid composition has an acid value of greater than 190. In other embodiments, the free conjugated linoleic acid composition has an acid value of from about 190 to 210. In some embodiments, the mild acid washes have a pH of from about 5 to 7. The present invention is not limited to any particular starting oil. Indeed, the composition comprising esters of linoleic acid is derived from an oil selected from the group consisting of safflower, sunflower, and corn oil. The present invention is not limited to the use of any particular alcoholate catalyst. Indeed, the alcoholate catalyst is selected from the group consisting of sodium methylate, potassium methylate, sodium ethylate and potassium ethylate.

In some embodiments, the present invention provides the conjugated linoleic acid composition produced by the method described in the preceding paragraph. In some embodiments, the composition has an acid value of greater than 190. In other embodiments, the composition has an acid value of from about 190–210. In still other embodiments, the composition is substantially free of esters of conjugated linoleic acid. In further embodiments, the composition comprises less than 1.0% trans-trans fatty acid isomers on molar basis. In some embodiments, food products or capsules comprising the conjugated linoleic acid compositions are provided.

In still other embodiments, the present invention provides methods of splitting saponified conjugated linoleic acids comprising: a) providing i) a composition comprising saponified conjugated linoleic acid and residual alcohol; and ii) a strong acid solution; b) injecting a strong acid solution into the saponified conjugated linoleic acid composition under conditions such that an oil phase comprising free conjugated fatty acids and a water phase comprising residual ethanol are produced; and c) immediately separating the oil phase and the water phase under conditions such that re-esterification between the residual ethanol and the conjugated fatty acids is substantially prevented. In some embodiments, the free conjugated linoleic acid composition has an acid value of greater than 190. In other embodiments, the free conjugated linoleic acid composition has an acid value of from about 190 to 210. In some embodiments, the strong acid solution has a pH of from about 2 to 3. The present invention is not limited to any particular starting oil. Indeed, the composition comprising esters of linoleic acid is derived from an oil selected from the group consisting of safflower, sunflower, and corn oil. The present invention is not limited to the use of any particular alcoholate catalyst. Indeed, the alcoholate catalyst is selected from the group consisting of sodium methylate, potassium methylate, sodium ethylate and potassium ethylate.

In some embodiments, the present invention provides the conjugated linoleic acid composition produced by the method described in the preceding paragraph. In some embodiments, the composition has an acid value of greater than 190. In other embodiments, the composition has an acid value of from about 190–210. In still other embodiments, the composition is substantially free of esters of conjugated linoleic acid. In further embodiments, the composition comprises less than 1.0% trans-trans fatty acid isomers on molar basis. In some embodiments, food products or capsules comprising the conjugated linoleic acid compositions are provided.

In some embodiments, the present invention provides methods for producing conjugated linoleic acid with a high acid value comprising: a) providing: i) a composition comprising esters of linoleic acid; and ii) an alcoholate catalyst; b) treating the composition comprising esters of linoleic acid with the alcoholate catalyst to produce a conjugated linoleic acid ester composition; c) treating the conjugated linoleic acid ester composition with alkali to produce a saponified conjugated linoleic acid composition comprising residual alcohol; d) removing the ethanol from the saponified conjugated linoleic acid composition; and e) treating the saponified conjugated linoleic acid composition with an acid solution to produce a free conjugated fatty acid composition. In some embodiments, the free conjugated linoleic acid composition has an acid value of greater than 190. In other embodiments, the free conjugated linoleic acid composition has an acid value of from about 190 to 210. In some embodiments, the strong acid solution has a pH of from about 2 to 3. The present invention is not limited to any particular starting oil. Indeed, the composition comprising esters of linoleic acid is derived from an oil selected from the group consisting of safflower, sunflower, and corn oil. The present invention is not limited to the use of any particular alcoholate catalyst. Indeed, the alcoholate catalyst is selected from the group consisting of sodium methylate, potassium methylate, sodium ethylate and potassium ethylate.

In some embodiments, the present invention provides the conjugated linoleic acid composition produced by the method described in the preceding paragraph. In some embodiments, the composition has an acid value of greater than 190. In other embodiments, the composition has an acid value of from about 190–210. In still other embodiments, the composition is substantially free of esters of conjugated linoleic acid. In further embodiments, the composition comprises less than 1.0% trans-trans fatty acid isomers on molar basis. In some embodiments, food products or capsules comprising the conjugated linoleic acid compositions are provided.

DEFINITIONS

As used herein, "conjugated linoleic acid" or "CLA" refers to any conjugated linoleic acid or octadecadienoic fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11, 13 octadecadienoic acid. As used herein, "CLA" encompasses a single isomer, a selected mixture of two or more isomers, and a non-selected mixture of isomers obtained from natural sources, as well as synthetic and semisynthetic CLA.

As used herein, the term "isomerized conjugated linoleic acid" refers to CLA synthesized by chemical methods (e.g., aqueous alkali isomerization, non-aqueous alkali isomerization, or alkali alcoholate isomerization).

As used herein, the term "conjugated linoleic acid moiety" refers to any compound or plurality of compounds containing conjugated linoleic acids or derivatives. Examples include, but are not limited to fatty acids, alkyl esters, and triglycerides of conjugated linoleic acid.

As used herein, it is intended that "triglycerides" of CLA contain CLA at any or all of three positions (e.g., SN-1, SN-2, or SN-3 positions) on the triglyceride backbone. Accordingly, a triglyceride containing CLA may contain any of the positional and geometric isomers of CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, propanol). Therefore, an ester of CLA or esterified CLA may contain any of the positional and geometric isomers of CLA.

It is intended that "non-naturally occurring isomers" of CLA include, but are not limited to c11,t13; t11,c13; t11,t13; c11,c13; c8,t10; t8, c10; t8,t10;c8,c10; and trans-trans isomers of octadecadienoic acid, and does not include t10,c12 and c9,t11 isomers of octadecadienoic acid. "Non-naturally occurring isomers" may also be referred to as "minor isomers" of CLA as these isomers are generally produced in low amounts when CLA is synthesized by alkali isomerization.

As used herein, "low impurity" CLA refers to CLA compositions, including free fatty acids, alkylesters, and triglycerides, which contain less than 1% total 8,10 octadecadienoic acids, 11,13 octadecadienoic acids, and trans-trans octadecadienoic acids.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid, while t10,c12 octadecadienoic acid or CLA refers to just the single isomer.

As used herein, the term "oil" refers to a free flowing liquid containing long chain fatty acids (e.g., CLA), triglycerides, or other long chain hydrocarbon groups. The long chain fatty acids, include, but are not limited to the various isomers of CLA.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "volatile organic compound" refers to any carbon-containing compound which exists partially or completely in a gaseous state at a given temperature. Volatile organic compounds may be formed from the oxidation of an organic compound (e.g., CLA). Volatile organic compounds include, but are not limited to pentane, hexane, heptane, 2-butenal, ethanol, 3-methyl butanal, 4-methyl pentanone, hexanal, heptanal, 2-pentyl furan, octanal.

As used herein, the term "metal oxidant chelator" refers to any antioxidant that chelates metals. Examples include, but are not limited to lecithin and citric acid esters.

As used herein, the term "alcoholate catalyst" refers to alkali metal compounds of any monohydric alcohol, including, but not limited to, potassium methylate and potassium ethylate.

DETAILED DESCRIPTION OF THE INVENTION

The compositions of the present invention result from a highly controlled isomerization process, and from using the preferred starting materials of sunflower, safflower, or corn oil. This composition has not heretofore been obtained, for application to an industrial scale, because the conventional processes historically produce conjugated linoleic acids for entirely different purposes, namely, as drying oils in the paint industry. Also, there has not been an appreciation of the implications of the isomer content of the final product, because the analytical methods for characterizing the fatty acids has not been widely available. Furthermore, the present invention provides a method for preventing oxidation of CLA during storage to form volatile organic compounds.

I. Methods for Conjugating Linoleic Acids

In the older isomerization processes, some of which are still in use in more modern format, production of the conjugated fatty acids was carried out in aqueous alkali (generally NaOH) at high temperatures in excess of 200° C. and usually at superatmospheric pressures. For example, U.S. Pat. No. 2,350,583 (Bradley) discloses an aqueous alkali process utilizing treated soaps in which both conjugation and polymerization occurred under rather harsh conditions at 200 to 250° C. for a period of several hours. The fractions of drying oil, starting with linseed oil, were obtained by distillation (see also Br. Pat. No. 558,881 for a very similar process). In a variation of the process, U.S. Pat. No. 4,381,264 teaches a process where a low water content reaction zone (0.5% water) contains stoichiometric base in the presence of $SO_2$ to obtain conjugation of the double bonds of various polyunsaturated fatty acids. The aqueous alkali process was adapted in U.S. Pat. No. 4,164,505 to a continuous flow process in which an alkali metal hydroxide and water are continuously charged in a flow zone maintained at between 200 and 370° C. At these temperatures, the time of reaction should be greatly foreshortened, but there is relatively little control over the isomerization. At the higher end of the temperature range, one skilled in the art would predict almost complete conversion to double trans species.

Methods of producing CLA using various nonaqueous solvents and catalysts have been described in the literature. Burr (U.S. Pat. No. 2,242,230) discloses the use of solvents such as methanol, butanol, ethanol and glycol in combination with various catalysts. These reaction parameters are summarized in Table 1. With the exception of glycol, the reactions were conducted either under reflux conditions or in sealed tubes. These reaction conditions result in imprecise control of two of the important reactions parameters-temperature and pressure. Imprecise control of these reactions parameters is likely to lead to less than complete conjugation and the formation of undesirable isomers.

TABLE 1

Patent 2,242,230

| Solvent | Catalyst | Temperature | Time |
| --- | --- | --- | --- |
| Ethanol | KOH, NaOH | reflux or higher* | varied |
| Butanol | KOH, NaOH | reflux or higher* | varied |
| Glycol | KOH | 195° C. | varied |
| Isoamyl Alcohol | KOH | reflux or higher* | varied |
| Butanol | Tributyl-amine | 140–175° C. | 22 hours |
| Butanol | Potassium Acetate | 175° C. | 36 hours |
| Butanol | Trisodium Phosphate | 175° C. | 36 hours |
| Butanol | Potassium Phosphate | 175° C. | 36 hours |
| Butanol | Sodium Benzoate | 175° C. | 36 hours |
| Butanol | Potassium Thiocyanate | 175° C. | 36 hours |
| Butanol | Borax | 175° C. | 36 hours |

Likewise, Baltes et al., (U.S. Pat. No. 3,162,658) disclose the use of nonaqueous solvents and various metallic bases as catalysts for the conjugation of fatty acids. The various reaction parameters of the methods described by Baltes et al. are summarized in Table 2. Baltes et al. also disclose the use of various low boiling point solvents. As most of these reactions were conducted at temperatures above the boiling point of the solvent employed, it is apparent that the reactions were conducted under pressure, which is an independent factor influencing the formation of octadecadienoic acid isomers. The product derived from these reactions will thus contain undesirable isomers.

TABLE 2

Patent 3,162,658

| Solvent | Catalyst | Temperature | Time |
|---|---|---|---|
| Methanol | KOH | 60–140° C. | variable |
| Methanol | Potassium Methylate | 140° C. | variable |
| Butanol | Potassium Methylate | 140° C. | variable |
| Ethanol | Potassium Methylate | 140° C. | variable |
| Isopropanol | Potassium Methylate | 120–140° C. | variable |
| Heptane/ 3° Butanol | Potassium Butylate | reflux | variable |
| 3° Butanol | Cesium Butylate | 140° C. | variable |
| Ethylene Diamine | Potassium Methylate | 140–160° C. | variable |
| Methanol | Sodium Amide | 140° C. | variable |

II. Isomerization with Alcoholate Catalysts

The CLA of the present invention lacks significant amounts of isomers such as the 8,10 isomer, the 11,13 isomer, and the various trans-trans isomers. These compositions were produced by a tightly controlled nonaqueous alkali isomerization process presented in flow diagram form in FIG. 1 and by isomerization with alkali alcoholate catalysts.

In preferred embodiments, esters of linoleic acid derived from sunflower oil, safflower oil, or corn oil are reacted in the presence of an alkali alcoholate catalyst and a small amount of a suitable solvent (e.g., methanol or ethanol). Accordingly, the present invention provides methods for producing alkyl esters of CLA. After fat splitting and dehydration of the seed oil, the free fatty acids are combined with methanol or another monohydric low molecular weight alcohol and heated to the temperature at which the alcohol boils. Esterification proceeds under refluxing conditions with removal of the reaction water through a condenser. The seed oil is refluxed with an excessive amount of alcohol and an alkali alcoholate catalyst for 2 hours at 65–78° C. while stirring. After separation of the layers, the bottom layer containing glycerol and excess alcohol is decanted. The esterification process can then be repeated with a smaller amount of alcohol and an alkali alcoholate catalyst to get an even more complete esterification. The ester is then washed with hot water with dissolved citric acid and dried under vacuum. In preferred embodiments, the esters are distilled prior to conjugation to remove glycerol and prevent formation of trimethoxypropane. Accordingly, the conjugated linoleic acid compositions of the present invention are substantially free of trimethoxypropane. By substantially free of trimethoxypropane it is meant that the final product contains less than 0.5% trimethoxypropane, more preferably less than 0.1% trimethoxypropane, and most preferably less than 0.05% trimethoxypropane.

In the esterification, methanol or ethanol are preferred, although other branched or straight chain monohydric alcohols may be used. The longer the aliphatic chain of the alkyl group, the more lipid compatible the material becomes. Also the viscosity tends to increase. For different types of feed or food, whose consistency varies, products of varying viscosity can be used to obtain the desired flow or compounding characteristics without affecting the therapeutic or nutritional properties arising from the CLA moieties. The theory and practice of esterification are conventional. A basic explanation of the most common methods is set forth in the McGraw-Hill Encyclopedia of Science & Technology, McGraw-Hill Book Co., N.Y.: 1996 (5th ed.). The animal and human body has a variety of esterases, so that the CLA-ester is cleaved to release the free fatty acids readily. Tissue uptake may have a different kinetics depending on the tissue involved and the benefit sought.

As described above, the preferred starting materials for conjugation with alcoholate catalysts are esters of linoleic acid derived from sunflower oil, safflower oil, and corn oil or other oils with a high linoleic acid content. Preferably the oils contain low levels of linolenic acid. Conjugation of linolenic acid results in the formation of several uncharacterized fatty acid moieties, the biological properties of which are unknown. Previous conjugation processes were not concerned with the production of unknown compounds because the products were used in drying oils, paints and varnishes and not in products destined from human or animal consumption. Accordingly, the CLA produced by those processes with oils containing high levels of linolenic acid were not suitable for nutritional uses.

In some embodiments, it is further contemplated that glycerol and esters of glycerol should be removed before making monoesters of fatty acids. Traces of glycerol present during conjugation contribute to the production of trimethoxypropane and triethoxypropane. Therefore, prior to conjugation, it is preferable to distill monoesters obtained by alcoholysis.

In preferred embodiments, isomerization is accomplished by reacting the esters of linoleic acid with a quantity of a monohydric alcohol (e.g., methanol, ethanol, propanol, or butanol) and an alcoholate catalyst (See, e.g., U.S. Pat. No. 3,162,658, incorporated herein by reference). Typical alcoholate catalysts are sodium or potassium ethoxide, or their methyl, butyl, or propyl counterparts (e.g., sodium methylate, potassium methylate, sodium ethylate and potassium ethylate). In some embodiments, the ratios of alcoholate catalyst and alcohol to the fatty acid esters is approximately 2–5% on a weight/weight basis, most preferably the ratios of alcoholate catalyst and alcohol to the fatty acid esters is about 2.8% on a weight/weight basis. For example, 100 kg of safflower fatty acid esters are mixed with 2.8 kg potassium ethoxide and 2.8 kg ethanol. In some embodiments, the resulting reaction mixture is stirred for about 2–10 hours, most preferably about 5 hours, at 100 to 130° C., most preferably at about 111–115° C. In some preferred embodiments, the reaction is conducted in a closed reaction vessel under nitrogen. This isomerization reaction produces conjugated linoleic acid alkyl esters.

In some preferred embodiments, the conjugated linoleic acid alkyl esters are converted to free fatty acids (i.e., free conjugated fatty acids). This is preferably accomplished by first saponifying the conjugated linoleic acid alkyl esters to produce a soap of conjugated linoleic acid and then splitting the soap by addition of an acid. In some embodiments, saponification is performed by reacting the alkyl esters of conjugated linoleic acid with an appropriate base. The present invention is not limited to the use of any particular base. Indeed, a variety of bases may be utilized, including, but not limited to, NaOH and KOH. Likewise, the present invention is not limited to the use of any particular acid. Indeed, a variety of acids may be utilized, including, but not limited to HCl, citric acid, and acetic acid.

The inventors unexpectedly discovered that during saponification and subsequent addition of acid to produce free fatty acids from a conjugated alkylester, the reverse reaction took place. Under certain circumstances, residual amounts of alcohol generated from the saponification of the alkylester (e.g., methanol or ethanol) react with the free fatty acids under acid conditions to produce esters (e.g., ethyl or methyl esters) of CLA. This results in a final product with an unacceptably low acid value. It is well known for those skilled in the art that esterification occurs between free fatty acids and alcohol if strong acids are used as catalysts. However, taking into account the low content of ethanol, an esterification was not expected to occur. The reason is probably that addition of acidic water does not remove ethanol from the free fatty acids layer as expected. CLA does probably due to polarity in the double bond region dissolve ethanol more easily than other fatty acids.

The present invention contemplates that the addition of several mild acid wash steps to the methods of CLA production using the isomerization with alcoholate catalysts disclosed herein is particularly useful in the batch production of CLA. Preferred embodiments of the present invention overcome the unexpected accumulation of esters (e.g., methyl esters or ethyl esters) of CLA during isomerization with alcoholate catalysts, by utilizing a plurality of (e.g., 1, 2, 3, or more) mild acid washes following the isomerization and saponification steps to ensure the removal of residual ethanol from the reaction mixture. It is contemplated that removal of residual amounts of ethanol prevents esterification reactions from taking place that produce ethyl ester derivatives of CLA. Preferably, the pH of the reaction mixture during the mild acid washes of the saponified CLA is kept from about 5 to 7. Suitable acids for use in the mild acid wash step include, but are not limited to, citric acid monohydrate, citric acid, or mild organic acids like acetic acid. The acids are mixed with a solvent (e.g., water) to produce a wash solution with a pH from about 5 to 7.

Examples 2 and 3 provide exemplary embodiments related to the mild acid washing steps described above. In particular, Example 2 describes the problem of ethyl ester production at batch scale production levels in certain embodiments of the alcoholate catalysts isomerization methods. Example 3 describes the addition of mild acid washing steps following isomerization and saponification steps in the alcoholate catalyst production methods at batch scale production levels.

In some embodiments, an in-line process may be used for soap splitting instead of a batch process. In these embodiments, a CLA soap stream is passed from a batch reactor into an inline reaction chamber for addition of a diluted acid solution (preferably having a pH of from about 2 to 3). A high speed mixer is used to split the CLA soap into free fatty acids. Small amounts of soap could potentially facilitate formation of an emulsion. Therefore, in addition to high speed mixing with the dilute acid, the temperature should preferably be maintained at about 80 to 90° C. From the acid addition reaction chamber, a stream containing the oil and water phases is immediately passed (e.g., within less than about 20 seconds after acid addition) into a centrifugal separator, where the oil and water are separated. The oil preferably contains a small amount of water at this stage in order to minimize loss of oil in the water phase. The temperature at this stage should still be maintained at from about 80 to 90° C. to facilitate rapid and complete splitting of the soap and to minimize emulsion problems.

In other alternative embodiments, the saponified CLA may be hydrolyzed enzymatically. Preferred enzymes include, but are not limited to, Novozym 435 and any other enzyme that is non-specific for triacylglycerol synthesis or hydrolysis (i.e., esterifies/hydrolyze all hydroxygroups (sn-1,sn-2 and sn-3) of glycerol). In still other alternative embodiments, the re-esterification reaction is substantially prevented by removing residual ethanol prior to treatment with acid. In preferred embodiments, the ethanol is removed from the soap by vacuum suction.

The compositions resulting from the processes described above may have a slightly yellow color due to residual soap and the presence of dimers. Accordingly, in some preferred embodiments, the resulting conjugated fatty acid composition is distilled to remove any impurities. In preferred embodiments, the finally product is essentially colorless and substantially free of contaminants such as dimmers or soaps. In preferred embodiments, the conjugated fatty acid compositions contain less then 10 ppm soap and/or less than 0.1% dimmers on a weight/weight basis as compared to conjugated fatty acid content. In preferred embodiments, the acid value of the final CLA composition produced by the methods described above is greater than 190, preferably ranging from about 190 to 210. Furthermore, the final product is substantially free of esters of CLA. By substantially free, it is meant that the concentration of ethyl esters CLA is less than about 1.0% of the concentration of free conjugated linoleic acid on a molar basis, and preferably less than 0.5% of the concentration of free conjugated linoleic acid on a molar basis. In preferred embodiments, the resulting composition contains less than 1.0% trans-trans fatty acids as compared to other fatty acids on a molar basis, and preferably less than 0.5% trans-trans fatty acids as compared to other fatty acids on a molar basis.

The free conjugated linoleic acids produced by these methods are suitable for a variety of uses. For example, the CLA may be used a dietary supplement, incorporated into food products, or formulated for oral delivery as described in more detail below. The CLA may also be utilized for the production of acylglycerols, preferably diacylglycerols of triacylglycerols, for oral administration or incorporation into food products or powders.

III. Stabilization of CLA Compounds

The present invention also contemplates stabilization of CLA containing compounds, including but not limited to, CLA, esters of CLA, and triglycerides of CLA by preventing oxidation of the compounds. The present invention is not limited to any one mechanism. Indeed, an understanding of the mechanism of the invention is not necessary to produce the composition or perform the methods of the present invention. Nevertheless, unlike non-conjugated fatty acids, CLA does not appear to form peroxide breakdown products. This was demonstrated experimentally by measuring peroxide values (PV) spectrophotometrically by a chlorimetric ferric thiocyanate method. After storage in open glass, the PV of CLA was 32; in comparison, the value for linoleic acid was 370.

CLA forms volatile organic compounds during breakdown, including hexane. Products stored in a steel drum for several weeks were found to contain up to 25 ppm hexane. Hexane has a characteristic taste and smell that is undesirable in food products. Oxidation of CLA appears to be caused by the presence of metal contaminants. Thus, a system for removal of such compounds that promote oxidation during purification is advantageous.

Furthermore, it is also advantageous to add compounds to CLA preparations to decrease oxidation during storage. Compounds that prevent oxidation (antioxidants) have two general mechanisms of action. The first is the prevention of oxidation by lipid peroxide radical scavenging. Examples include but are not limited to tocopherols and ascorbylpalmitate. The second mechanism for preventing oxidation is by the chelation of metal ions. Examples of metal oxidant chelators include, but are not limited to, citric acid esters and lecithin. Some commercially available compounds (e.g., Controx, Grunau (Henkel), Illertissen, Del.) include both peroxide scavengers and metal chelators (e.g., lecithin, tocopherols, ascorbylpalmitate, and citric acid esters). In some embodiments of the present invention, metal oxidant chelators are added to CLA containing compounds to prevent oxidation. In other embodiments, a combination of metal oxidant chelators and peroxide scavengers is included in the CLA composition.

In some embodiments, gas chromatography/mass spectroscopy is used in detect the presence of volatile organic breakdown products of CLA. In other embodiments, oil stability index (OSI) measurements are used to detect the presence of volatile organic breakdown products of CLA. In some embodiments of the present invention methods for the removal of pro-oxidants (e.g., iron) from CLA samples are provided. Methods include, but are not limited to distillation or by adsorption. In some embodiments of the present invention, compounds are added to prevent oxidation of CLA. Examples of volatile organic compounds include pentane, hexane, heptane, 2-butenal, ethanol, 3-methyl butanal, 4-methyl pentanone, hexanal, heptanal, 2-pentyl furan, and octanal. It is understood by one skilled in the art that samples may contain additional volatile organic compounds, depending on the starting materials and the exact reaction conditions.

In preferred embodiments, precautions are taken during purification to prevent oxidation during storage. These precautions include the removal of compounds that serve as pro-oxidants, including but not limited to iron or other metals. In some embodiments, metals are removed by treating with adsorbing agents, including but not limited to bleaching earth, active charcoal zeolites, and silica. In other embodiments, the pro-oxidants are removed by distillation. In some embodiments, silica is used as the adsorbing agent. In other embodiments, pro-oxidants are removed in a distillation process. In some embodiments, oxidation of CLA is prevented by the addition of metal oxidant chelators or peroxide scavengers to the finished product. In some embodiments, the amount of oxidation is measured by the oil stability index (OSI). The OSI (See e.g., AOCS official method Cd 12b–92) is a measurement of an oil's resistance to oxidation. It is defined mathematically as the time of maximum change of the rate of oxidation. This rate can be determined mathematically. Experimentally, the OSI is calculated by measuring the change in conductivity of deionized water is which volatile organic acids (oxidation products) are dissolved. When performing OSI measurements, it is important to avoid contamination by trace amounts of metals, which can accelerate the oxidation process. This is generally accomplished by careful washing of all glassware used with a cleaning solution lacking chromate or surfactants. Water must be deionized and all solvents must be of a highly purified grade.

IV. Administration of CLA Containing Compounds

The conjugated linoleic moieties of the present invention may be provided in a variety of forms. In some embodiments, administration is oral. The CLA moieties may be formulated with suitable carriers such as starch, sucrose or lactose in tablets, pills, dragees, capsules, solutions, liquids, slurries, suspensions and emulsions. Preferably, the CLA formulations contain antioxidants, including, but not limited to Controx, Covi-OX, lecithin, and oil soluble forms of vitamin C (ascorbyl palmitate). The CLA may be provided in aqueous solution, oily solution, or in any of the other forms discussed above. The tablet or capsule of the present invention may be coated with an enteric coating which dissolves at a pH of about 6.0 to 7.0. A suitable enteric coating which dissolves in the small intestine but not in the stomach is cellulose acetate phthalate. In some embodiments, the CLA is provided as soft gelatin capsules containing about 750 mg CLA. The CLA may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of Remington's Pharmaceutical Sciences (Maack Publishing Co., Easton, Pa.).

An effective amount of a CLA moiety (in free fatty acid, alkyl ester, or acylglycerol form) may also be provided as a supplement in various food products, including animal feeds, and drinks. For the purposes of this application, food products containing CLA means any natural, processed, diet or non-diet food product to which exogenous CLA has been added. The CLA may be added in the form of free fatty acids, esters of conjugated linoleic acid, or as an oil containing partial or whole triglycerides of CLA. Therefore, CLA may be directly incorporated into various prepared food products, including, but not limited to diet drinks, diet bars, supplements, prepared frozen meals, candy, snack products (e.g., chips), prepared meat products, milk, cheese, yogurt and any other fat or oil containing foods. Food products formulated with alkyl esters or conjugated linoleic acid moieties produced by alkali alcoholate catalysts contain alcohols (e.g., methyl or ethyl alcohol) depending on the solvents and catalysts utilized. Generally, the alcohols will be present at about 1 to 10 ppm.

Furthermore, as shown above and in the Examples, CLA compositions can contain levels of volatile organic compounds that cause the taste and smell of food products containing the CLA to be adversely effected. It is contemplated that the food products of the present invention that contain CLA compositions having less than 100 ppm volatile organic compounds, and preferably less than 5 ppm volatile organic compounds, are superior in taste and smell to food products containing higher levels of volatile organic compounds and will be preferred in blind taste and smell tests. Accordingly, some embodiments of the present invention provide a food product containing a conjugated linoleic acid moiety, wherein the conjugated linoleic acid moiety has a sufficiently low volatile organic acid compound concentration so that taste and smell of the food product is not affected.

Experimental

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); µM (micromolar) kg (kilograms); g (grams); mg (milligrams); µg (micrograms); ng (nanograms); L or l (liters); ml (milliliters); µl (microliters); cm (centimeters); mm (millimeters); m (nanometers); ° C. (degrees centigrade); KOH (potassium hydroxide); HCL (hydrochloric acid); Hg (mercury).

EXAMPLE 1

Large Scale Batch Production of Conjugated Safflower FAME

The production of safflower conjugated FAME may be divided into two steps, methanolysis and conjugation. For methanolysis, 6,000 kg safflower oil was drawn into a closed reactor. The reactor was purged with nitrogen at atmospheric pressure, and 1150 liters of methanol and 160 kg of NaOCH$_3$ (30% solution) were added. The mixture is heated to 65° C. while stirring, and reacted at 65° C. for 2 hours. The resulting bottom layer was decanted while the reactor was purged with nitrogen gas. 1000 liters of water (40–50° C., into which 50 kg citric acid monohydrate has been dissolved) was then added while stirring. The layers were allowed to separate (approx. 60 min.) and the bottom layer decanted while purging the reactor with nitrogen gas. The resulting safflower FAME product was dried at 80° C. under vacuum for one hour. A similar procedure may be used to produce ethyl esters (See Example 4).

EXAMPLE 2

Batch Production Method with Low pH Wash

This example describes a batch scale production method with unexpectedly low acid value final products. 35 kg of an ethyl ester of CLA was saponified in a 350 l reaction vessel using 9.8 kg of KOH dissolved in 14.5 kg of water. The temperature was kept at 75° C. for 1 hour. Slight overpressure (0.2 bar) was used to prevent soap forming during the slight increase in temperature due to the exothermic saponification reaction. After the reaction was complete, 10 l of water was added to facilitate stirring the high viscosity mixture. Hydrochloric acid, 17.5 l, was added to the mixture whil stirring and the mixture was heated to 80° C. Free fatty acids were formed and the bottom layer was drained off. The bottom layer pH was below about 3.0–2.0. Five kg of citric acid was dissolved in 50 kg of water and added to the reactor while stirring. The temperature was raised to 90° C. to avoid emulsions. Another 5 kg of citric acid was added after draining off the water to split all traces of soap. The resulting acid value of the final product was about 186, which was less than the expected 200 value.

EXAMPLE 3

Batch Production Method with Mild Acid Wash

This example describes a batch scale production method using a series of mild acid washes. 75.0 kg of ethyl ester of safflower oil was isomerized using 1.5 kg of potassium ethoxide. For saponification, the ethyl ester was treated with 16.6 kg of KOH dissolved in 32 l of water. The temperature of the mixture was held at between 75–80° C., and the reaction was kept in a nitrogen atmosphere under 0.3 bar of pressure. The temperature in the exothermic reaction mixture increased to 85° C. After the saponification reaction was complete, 8.0 kg of citric acid monohydrate (solid) was added under vigorous stirring and free fatty acids were formed. The bottom phase water with a pH of 6 was drained off. Next, 2 water washes were sprayed into the reactor without stirring and allowed to settle before being drained off. Next, 3 final washes with citric acid monohydrate dissolved in water were performed while vigorously stirring the reaction mixture. These three final washes were 1.0, 2.0, and 7.0 kg, respectively. The oil product was dried under vacuum. The acid value of the product was 201.

EXAMPLE 4

Laboratory Synthesis of Conjugated Safflower FAEE

The formation of ethyl esters from safflower oil was accomplished by mixing 1000 g of safflower oil with 50 ml of 21% sodium ethylate in ethanol solution and 230 ml of pure ethanol in a round bottom flask. The mixture was refluxed for 1 hour at 78° C. while stirring, and then transferred to a separatory funnel. After separation of the layers, the bottom layer, 100 ml was decanted. The top layer containing the ethyl esters was washed 3 times with hot water, 90° C., and then dried under vacuum. The dried ethyl esters were then distilled under vacuum (approx 0.3 mbar) at 180° C.

Conjugation of the distilled FAEE from safflower oil to produce a CLA FAEE product was carried out by mixing 100 g FAEE with 2.00 g sodium ethylate powder and 0.66 g ethanol in a minireactor. The air was replaced with nitrogen and the reactor was then heated to 120° C. After the mixture had been stirred for 3 hours at 120° C. the reactor was cooled to 80° C. The conjugated oil was then washed 5 times with 50 g of hot water, 80–90° C. Washing water no. 4 contained 2 g of dissolved citric acid. The ethyl ester was then dried under vacuum. Final acid value of the CLA ethyl ester was 0.9. The residual amount of non-conjugated linoleic acid was 0.9%.

What should be clear from above is that the present invention provides a conjugated linoleic acid composition of high purity that can be used in the formulation of animal feeds and in food products suitable for human consumption.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in medicine, biochemistry, or related fields are intended to be within the scope of the following claims.

The invention claimed is:

1. A method for producing conjugated linoleic acid with a high acid value comprising:
   a) providing:
      i) a composition comprising esters of linoleic acid; and
      ii) an alcoholate catalyst;
   b) treating said composition comprising esters of linoleic acid with said alcoholate catalyst to produce a conjugated linoleic acid ester composition;

c) treating said conjugated linoleic acid ester composition with alkali to produce a saponified conjugated linoleic acid composition; and d) treating said saponified conjugated linoleic acid composition with a mild acid wash to produce a free conjugated fatty acid composition containing at least about 0.5% esters of conjugated linoleic acids.

2. The method of claim 1, wherein said free conjugated linoleic acid composition has an acid value of greater than 190.

3. The method of claim 1, wherein said free conjugated linoleic acid composition has an acid value of from about 190 to 210.

4. The method of claim 1, wherein said mild acid wash has a pH of from about 5 to 7.

5. The method of claim 1, wherein step (d) further comprises a plurality of mild acid washes.

6. The method of claim 1, wherein said mild acid wash is performed with a citric acid solution.

7. The method of claim 1, wherein said composition comprising esters of linoleic acid is derived from an oil selected from the group consisting of safflower, sunflower, and corn oil.

8. The method of claim 1, wherein said alcoholate catalyst is selected from the group consisting of sodium methylate, potassium methylate, sodium ethylate and potassium ethylate.

9. The method of claim 1, wherein said alcohol is ethanol.

10. The conjugated linoleic acid composition produced by the method of claim 1.

11. The conjugated linoleic acid composition of claim 10, wherein said composition has an acid value of greater than 190.

12. The conjugated linoleic acid composition of claim 10, wherein said composition has an acid value of from about 190–210.

13. The conjugated linoleic acid composition of claim 10, wherein said composition contains between about 0.5% and 1% esters of conjugated linoleic acid.

14. The conjugated linoleic acid composition of claim 10, wherein said composition comprises less than 1.0% trans-trans fatty acid isomers on molar basis.

15. A food product comprising the conjugated linoleic acid composition of claim 10.

16. A capsule containing the conjugated linoleic acid composition of claim 10.

* * * * *